(12) United States Patent
Gao et al.

(10) Patent No.: US 9,200,323 B2
(45) Date of Patent: Dec. 1, 2015

(54) HYBRIDIZATION METHODS USING NATURAL BASE MISMATCHES

(75) Inventors: Huafang Gao, Beijing (CN); Ze Li, Beijing (CN); Dong Wang, Beijing (CN); Yanhua Liu, Beijing (CN); Xiang Liu, Beijing (CN); Yangzhou Jiang, Beijing (CN); Li Li, Beijing (CN); Chuanzan Zhao, Beijing (CN); Gengxin Lan, Beijing (CN); Tao Guo, Beijing (CN); Bin Cai, Beijing (CN); Jing Cheng, Beijing (CN)

(73) Assignees: CapitalBio Corporation, Beijing (CN); Tsinghua University, Beijing (CN)

( * ) Notice: Subject to any disclaimer, the term of this patent is extended or adjusted under 35 U.S.C. 154(b) by 1068 days.

(21) Appl. No.: 12/162,286

(22) PCT Filed: Feb. 6, 2007

(86) PCT No.: PCT/CN2007/000402
§ 371 (c)(1),
(2), (4) Date: Nov. 26, 2008

(87) PCT Pub. No.: WO2007/090345
PCT Pub. Date: Aug. 16, 2007

(65) Prior Publication Data
US 2009/0156419 A1 Jun. 18, 2009

(30) Foreign Application Priority Data
Feb. 8, 2006 (CN) .......................... 2006 1 0002863

(51) Int. Cl.
*C12Q 1/68* (2006.01)
(52) U.S. Cl.
CPC ............ *C12Q 1/6881* (2013.01); *C12Q 1/6832* (2013.01); *C12Q 2600/156* (2013.01)
(58) Field of Classification Search
None
See application file for complete search history.

(56) References Cited

U.S. PATENT DOCUMENTS

| 5,780,233 A * | 7/1998 | Guo et al. ........................ 435/6 |
| 6,352,828 B1 | 3/2002 | Brenner |
| 6,518,025 B1 * | 2/2003 | Steinborn et al. ................. 435/6 |

FOREIGN PATENT DOCUMENTS

| EP | 1 130 119 | 9/2001 |
| WO | WO-93/19201 | 9/1993 |
| WO | WO-97/46711 | 12/1997 |

OTHER PUBLICATIONS

Bhaumik et al., J. Biomol. Struct. Dyn. (2002) 20(2):199.
Fang et al., Nucleic Acids Res. (2001) 29(15):3248.
Guo et al., Nat. Biotechnol. (1997) 15:331-5.
Igloi, PNAS USA (1998) 95:8562.
Ikuta et al., Nucleic Acids Res. (1987) 15(2):797.
International Search Report for PCT/CN2007/000402, mailed on May 17, 2007, 4 pages.
Kawase et al., Nucleic Acids Res. (1986) 14(19):7727.
Letowski et al., J. Microbiol. Methods (2004) 57(2):269.
Petersen et al., Trends in Biotechnology (2003) 21(2):74-81.
Written Opinion of the International Searching Authority for PCT/CN2007/000402, mailed on May 17, 2007, 4 pages.
Zhang et al., Biophysical J. (2001) 81(2):1133.
Burgner et al., Nucleosides, Nucleotides and Nucleic Acids (2004) 23(5):755-765.
Supplementary European Search Report for EP 07710869.4, mailed Dec. 29, 2009, 9 pages.

* cited by examiner

*Primary Examiner* — James Martinell
(74) *Attorney, Agent, or Firm* — Morrison & Foerster LLP

(57) ABSTRACT

The present invention provides an improved nucleic acid hybridization process employing a modified oligonucleotide probe comprising naturally occurring nucleotide bases. At least one nucleotide in the modified oligonucleotide is artificially mismatched relative to the control nucleic acid in addition to any mismatches arising from a variant nucleic acid target containing a sequence variation. The artificial mismatch and the sequence variation positions are separated from one another on the oligonucleotide by six to nine nucleotide positions.

18 Claims, 4 Drawing Sheets

```
                   -9 -8 -7 -6 -5 -4 -3 -2 -1 0 1 2 3 4 5 6 7 8 9
Probe Sequence:  5'-G G C T A T C C G A T C C T G G C C T-3'
Target Sequence: 3'-C C T A T A G G C T A G G A C C G G A-5'
```

HYBRIDIZATION METHODS USING NATURAL BASE MISMATCHES

CROSS-REFERENCE TO RELATED APPLICATIONS

This application is the national phase of PCT application PCT/CN2007/000402 having an international filing date of Feb. 6, 2007, which claims priority from China application number 200610002863.8 filed Feb. 8, 2006. The contents of these documents are incorporated herein by reference.

TECHNICAL FIELD

Reference to Sequence Listing Submitted Via EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 514572003000Seqlist.txt | Mar. 31, 2011 | 7,504 bytes |

The present invention relates to the field of molecular biology and more particularly to the field of nucleic acid hybridization.

BACKGROUND ART

Sequence specific oligonucleotide probes (SSOP) can be used to identify nucleic acid sequences. Because the thermodynamic stability of matched duplexes is higher than a mismatched duplex, matched and mismatched duplexes can be identified by setting different hybridization temperatures and conditions.

Although hybridization techniques can be a useful tool for correctly identifying a complementary strand, current hybridization methods suffer from various limitations. For example, mismatch discrimination is affected by different mismatched base pairs, nucleic acid sequences, nucleic acid structures, etc. (See, Kawase et al., Nucleic Acids Res. 14(19):7727 (1986); Ikuta et al., Nucleic Acids Res. 15(2):797 (1987); Zhang et al., Biophysical J., 81(2):1133 (2001); Fang et al., Nucleic Acids Res. 29(15):3248 (2001)). The stability difference between a perfectly matched complement and a complement mismatched at only one base can also be quite small, corresponding to as little as 0.5° C. difference in their $T_m$ value (Guo et al., Nat. Biotechnol. 15:331-5 (1997); and U.S. Pat. No. 5,780,233 to Guo et al.).

Some methods have been used to enhance the discrimination of single-base mismatches, such as the use of short probes having a length of no more than 15 nt. However, shorter probes are limited by their poor sequence specificity and low hybridization efficiency. In addition, the mismatch identification was also affected by GC percent, and the number and site of mismatched base. (See, Bhaumik et al., J Biomol Struct Dyn., 20(2):199 (2002); Letowski et al., J Microbiol Methods, 57(2):269 (2004)).

Alternatively, chemically modified nucleic acids such as locked nucleic acids (LNA) and peptide nucleic acids (PNA) may be used to enhance the discrimination of single-base mismatches. Locked nucleic acids (LNA) are oligonucleotide analogues containing a conformationally restricted nucleotide with a 2'-O, 4'-C-methylene bridge that induces thermal affinities when mixed with complementary single stranded DNA and RNA. (See, Petersen et al., Trends in Biotechnology, 21 (2): 74-81). Peptide nucleic acids (PNA) are synthetic chimeras of nucleobases linked to a peptide backbone. This spacing permits the bases to form, among other possible structures, standard base pairs with natural nucleic acids. However, the lack of the phosphodiester linkage, leading to an electronically neutral species, has important consequences for the base-pairing potential of PNA. Investigations of the stability and kinetics of PNA-DNA (and -RNA) duplex formation have confirmed and quantified the existence of strong base-pairing interactions under various conditions (See, Gabor, Proc. Natl. Acad. Sci. 95: 8562 (1998)).

In other methods, some base analogs such as 3-nitropyrrole, were inserted into oligonucleotide probes to increase the differences in thermal stability between hybrids formed with normal and single-nucleotide-variant DNA targets (See, Guo et al., Nat. Biotechnol., 15:331 (1997)).

However, existing methods used to enhance the discrimination of single-base mismatches are expensive because LNA, PNA and other base analogs are expensive to synthesize. Furthermore, optimal conditions such as the optimum number and site for these modified nucleic acids in an oligonucleotide probe are not known. Thus, there remains a need for improved low-cost methods for increasing hybridization specificity, and for enhancing the role of SSOP in the gene sequence analysis.

DISCLOSURE OF THE INVENTION

The present invention generally relates to hybridization methods using a probe comprising naturally occurring nucleotides wherein at least one nucleotide is artificially mutated. The probes for use in the methods of the present invention are highly specific, and may be easily synthesized. The probes are also inexpensive, thereby providing improved low-cost methods for increasing hybridization specificity.

More particularly, the artificially mutated probe comprises a sequence complementary to the target nucleic acid molecule, and includes at least one nucleotide that is artificially mismatched relative to a control nucleic acid in addition to any mismatches arising from a variant nucleic acid target containing a sequence variation. The artificial mismatch and the sequence variation positions are separated from one another on the oligonucleotide by six to nine nucleotide positions.

The artificial mismatch in the sequence specific oligonucleotide probe encompass but are not limited to base substitution, deletion, and insertion. Under proper hybridization condition, this probe hybridizes with a target nucleotide sequence but not with other nucleotide sequences, thereby preventing false positive or negative results. In one embodiment, the mutation site is near the probe ends.

In another embodiment, the length of the sequence specific oligonucleotide probe ranges from 11 to 70 nucleotides, or more particularly, from 15 to 25 nucleotides.

Suitable bases for preparing the oligonucleotide probes of the present invention may be selected from naturally occurring nucleotide bases such as adenine, cytosine, guanine, uracil, and thymine.

Alternatively, nonnaturally occurring or synthetic nucleotide bases may be used to practice the methods of the invention. Examples of such bases include but are not limited to 8-oxo-guanine, 6-mercaptoguanine, 4-acetylcytidine, 5-(carboxyhydroxyethyl) uridine, 2'-O-methylcytidine, 5-carboxymethylamino-methyl-2-thioridine, 5-carboxymethylaminomethyl uridine, dihydrouridine, 2'-O-methylpseudouridine, beta-D-galactosylqueosine, 2'-Omethylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, beta-D-mannosylqueosine, 5-methoxycarbonylmethyluridine, 5-methoxyuridine, 2-methylthio-N6-isopentenyladenosine, N-((9-beta-D-ribofuranosyl-2-methylthiopurine-6-yl)carbamoyl)threonine, N-((9-beta-D-ribofuranosylpurine-6-yl) N-methylcarbamoyl) threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methyluridine, N-((9-beta-D-ribofuranosylpurine-6-yl) carbamoyl) threonine, 2'-O-methyl-5-methyluridine, 2'-O-methyluridine, wybutosine, and 3-(3-amino-3-carboxypropyl) uridine, except 1-(2'-Deoxy-beta-D-ribofuranosyl)-3-nitropyrrole.

MODES OF CARRYING OUT THE INVENTION

Figures 1, 2:
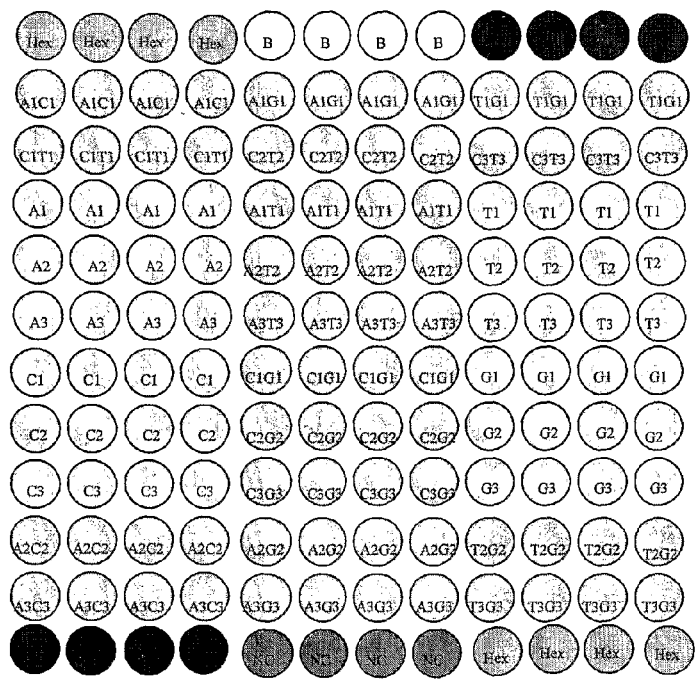
FIG. 1 (SEQ ID NOS:19-20) shows an SNP of a target nucleotide sequence.
FIG. 2 depicts a microarray spot pattern for oligonucleotides described in Example 1.

The present invention generally relates to hybridization methods using a probe comprising naturally occurring nucleotides wherein at least one nucleotide is artificially mutated.

In one aspect, the present invention provides a process for hybridizing an oligonucleotide to a first nucleic acid target, the method comprising the steps of: providing an oligonucleotide having a nucleic acid sequence complementary in part to the first target, but comprising at least one artificial mismatch relative to the first target and having a nucleic acid sequence complementary in part to a second target, but comprising at least one artificial mismatch and a true mismatch relative to the second target; where the true mismatch and the artificial mismatch are separated from one another by six to nine nucleotide positions and where the artificial mismatch is a naturally occurring nucleotide base; and combining the oligonucleotide and the first target under selected hybridization conditions to form a first duplex.

In another aspect, the present invention provides a process for discriminating between a first nucleic acid target and a second nucleic acid target in a test sample wherein the second nucleic acid target has a sequence variation relative to the first target, the process comprising the steps of: providing an oligonucleotide having a nucleic acid sequence complementary in part to the first target, including at the position of the sequence variation, but comprising an artificially mismatched naturally occurring nucleotide base relative to the targets at a position other than that of the sequence variation, the artificially mismatched base and the sequence variation positions being separated from one another on the oligonucleotide by six to nine nucleotide positions; combining the oligonucleotide and the test sample under selected hybridization conditions to form a product from the group consisting of (a) a first duplex comprising the oligonucleotide and the first target, (b) a second duplex comprising the oligonucleotide and the second target and being less stable than the first duplex, and (c) a mixture comprising both the first duplex and the second duplex; selectively detecting the first duplex comprising the oligonucleotide and the first target or the second duplex comprising the oligonucleotide and the second target.

As used herein, a "sequence variation" or "variant" encompasses any change in a target sequence relative to a control or normal nucleic acid target. The difference can be as subtle as a single nucleotide polymorphism, but can also include two or more adjacent or non-adjacent single nucleotide changes, as well as more pronounced changes from the control that can include nucleic acid insertions, deletions, and rearrangements. Such insertions and deletions can be as small as 1 nucleotide, and no upper limit on insertion or deletion size is expected, if the oligonucleotide probe or primer is properly designed.

In the present methods, the greatest $\Delta T_m$ is observed when a single artificial mismatch of a naturally occurring modified nucleotide is introduced six to nine bases away from the true mismatch. At such optimum spacing, the $\Delta T_m$s are increased by 4-10 degrees Celsius, thereby providing improved discrimination.

The following examples are provided to illustrate the present methods, without limiting the scope of the invention.

In the Examples below, there are 12 types of mismatches for each base pair, including A/A, A/C, A/G, T/T, T/C, T/G, C/C, C/A, C/T, G/G, G/A, G/T. FIG. 1 shows the site of each nucleotide, wherein the SNP site of the target nucleotide sequence is identified at the zero position. All the other nucleotide sites may be modified employing artificial mutations.

Example 1

Three HLA sequences (69 bp) with different $T_m$ values ($T_m$ value of sequence 1>2>3) were detected using a normal probe and an artificially mutated probe with a base inserted at the position between 5$^{th}$ and 6$^{th}$ base from 3' end of the probe. The SNP site in each sequence is shown in lower case letter and underlined.

HLA Sequence 1
A1: 5'-GGCATCAGGCCGCCCCAGCTCCGTCACCGCCCGGaACTCCCCC
ACGTCGCTGTCGAAGCGCACGGACTC-3'
(SEQ ID NO: 1)

-continued

```
T1: 5'-GGCATCAGGCCGCCCCAGCTCCGTCACCGCCCGGtACTCCCCC
    ACGTCGCTGTCGAAGCGCACGGACTC-3'
    (SEQ ID NO: 2)

C1: 5'-GGCATCAGGCCGCCCCAGCTCCGTCACCGCCCGGcACTCCCCC
    ACGTCGCTGTCGAAGCGCACGGACTC-3'
    (SEQ ID NO: 3)

G1: 5'-GGCATCAGGCCGCCCCAGCTCCGTCACCGCCCGGgACTCCCCC
    ACGTCGCTGTCGAAGCGCACGGACTC-3'
    (SEQ ID NO: 4)

HLA Sequence 2
A2: 5'-TAGGTGTCCACCGCGGCCCGCCTCTGCTCCAGGAaGTCCTTCT
    GGCTGTTCCAGTACTCGGCATCAGGC-3'
    (SEQ ID NO: 5)

T2: 5'-TAGGTGTCCACCGCGGCCCGCCTCTGCTCCAGGAtGTCCTTCT
    GGCTGTTCCAGTACTCGGCATCAGGC-3'
    (SEQ ID NO: 6)

C2: 5'-TAGGTGTCCACCGCGGCCCGCCTCTGCTCCAGGAcGTCCTTCT
    GGCTGTTCCAGTACTCGGCATCAGGC-3'
    (SEQ ID NO: 7)

G2: 5'- TAGGTGTCCACCGCGGCCCGCCTCTGCTCCAGGAgGTCCTTCT
    GGCTGTTCCAGTACTCGGCATCAGGC-3'
    (SEQ ID NO: 8)

HLA Sequence 3
A3: 5'-AGTATCTGTCCAGGAACCGCACCCGCTCCGTCCCaTTGAAGAA
    ATGACACTCCCTCTTAGGCTGCCACA-3'
    (SEQ ID NO: 9)

T3: 5'-AGTATCTGTCCAGGAACCGCACCCGCTCCGTCCCtTTGAAGAA
    ATGACACTCCCTCTTAGGCTGCCACA-3'
    (SEQ ID NO: 10)

C3: 5'-AGTATCTGTCCAGGAACCGCACCCGCTCCGTCCCcTTGAAGAA
    ATGACACTCCCTCTTAGGCTGCCACA-3'
    (SEQ ID NO: 11)

G3: 5'-AGTATCTGTCCAGGAACCGCACCCGCTCCGTCCCgTTGAAGAA
    ATGACACTCCCTCTTAGGCTGCCACA-3'
    (SEQ ID NO: 12)

Normal probe:         5'-TAMRA-TGGGGGAGTtCCGG GCGGT
                         (SEQ ID NO: 13)

Artificial            5'-TAMRA-TGGGGGAGTtCCGGcGCGGT
mutated probe:           (SEQ ID NO: 14)
```

FIG. 2 shows the microarray spot pattern of the 69 nt oligonucleotides spotted on slides. These identifiers corresponding to A1, T1, C1, G1, A2, T2, C2, G2, A3, T3, C3 and G3 comprise only one kind of oligonucleotide, and represent a homozygote. Other spots, such as A1G1, comprise A1 and G1 two kinds of 69 nt oligonucleotides, and represent a heterozygote. Other spots named Hex, PC, NC and BC represent quantitative control, positive control, negative control and blank control of microarray, respectively.

Figure 3:
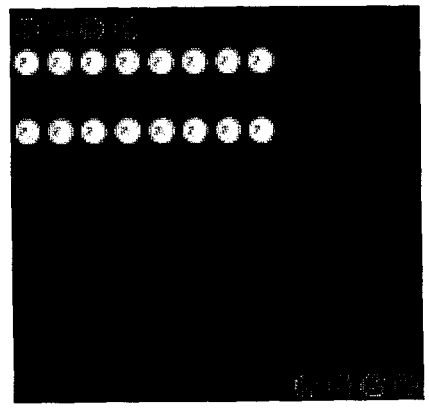
FIG. 3 shows the predicted hybridization pattern for oligonucleotides described in Example 1.
Figure 4A:
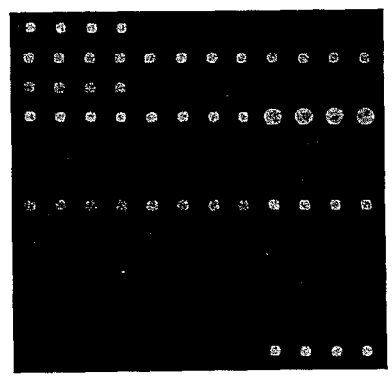
FIGS. 4A and 4B depict the hybridization of the microarrays shown in FIG. 1 using a normal probe and an artificial mutated probe, respectively.
Figure 4B:
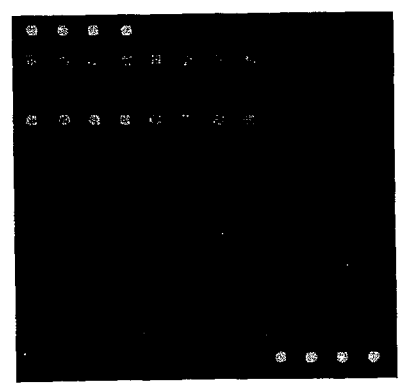

FIG. 4A and FIG. 4B show the hybridization results using a normal probe and an artificially mutated probe, respectively. In this example, the artificially mutated probe contains an artificially inserted cytosine ("c") when compared to the normal probe. Compared with the predicted hybridization pattern (as shown in the FIG. 3), FIG. 4A shows some cross hybridization with the normal probe. In contrast, the hybridization results in FIG. 4B has a 100% match with the predicted hybridization pattern.

Example 2

In this example, 52 standard HLA samples from International Histocompatibility Working Group (IHWG, located on the world wide web at ihwg.org/shared/cbankservices.htm#ssopref) were detected using a normal probe and an artificial mutated probe artificially substituted at the third base from 5' end of the probe.

```
Normal probe:        5'-TAMRA-GGAACACACGGAAAGTGAA-3'
                        (SEQ ID NO: 15)

Artificial mutated   5'-TAMRA-GGcACACACGGAAAGTGAA-3
probe:                  (SEQ ID NO: 16)
```

Figure 5:
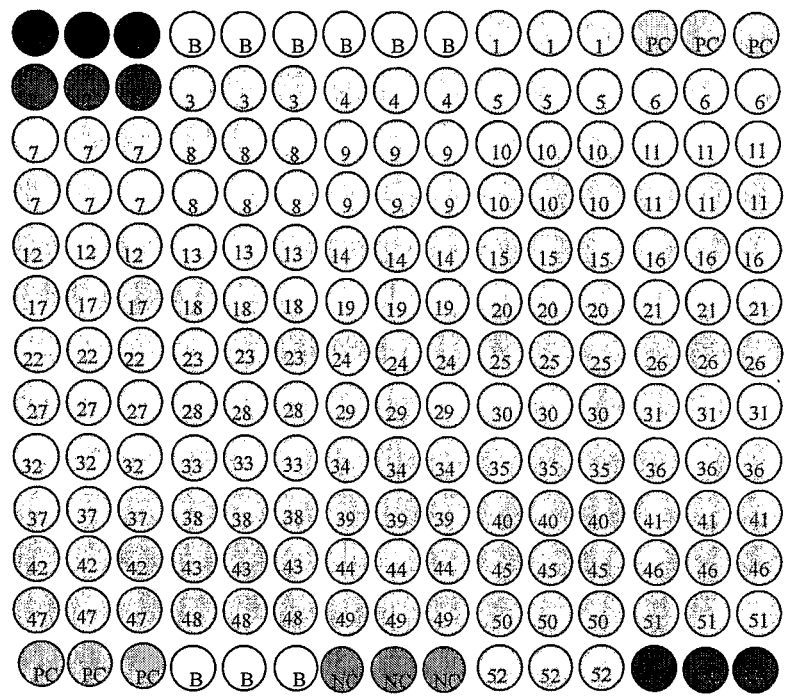
FIG. 5 depicts a microarray spot pattern for oligonucleotides described in Example 2.

FIG. 5 shows the microarray spot pattern of PCR samples from 52 standard HLA samples spotted on the slides. These spots named 1-52 represent 1-52 standard HLA samples, respectively. Other spots named Hex, PC, NC and BC represent quantitative control, positive control, negative control and blank control of microarray, respectively.

Figure 6:
FIG. 6 shows the predicted hybridization pattern for oligonucleotides described in Example 2.
Figure 7A:
FIGS. 7A and 7B depict the hybridization of the microarrays shown in FIG. 5 using a normal probe and an artificial mutated probe, respectively.
Figure 7B:
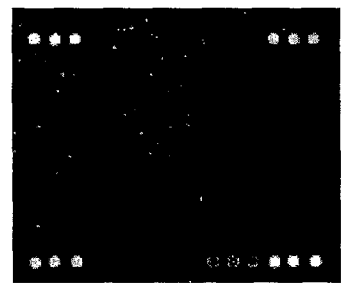

After hybridization, only the 52# HLA standard sample could be hybridized with probes. Other samples comprised at least one mismatched base for the probes. Compared with the predicted hybridization pattern (as shown in FIG. 6), FIG. 7A shows numerous cross hybridization with the normal probe. In contrast, the hybridization results using an artificial mutated probe in FIG. 7B shows a 100% match with the predicted results.

Example 3

In this example, standard DNAs from IHWG were detected using a normal probe and an artificially mutated probe wherein the artificial mutation site is separated from the natural SNP site by a 6-mer oligonucleotide.

```
Probe Sequence:                                          5' -TATTGGGACGGGGAGAgAC-3'
                                                            (SEQ ID NO: 17)

Alleles which perfectly matched with the probe           -------------------C--

Alleles which have one base mismatch with the probe:     ----------C--------C--
```

Figure 8:
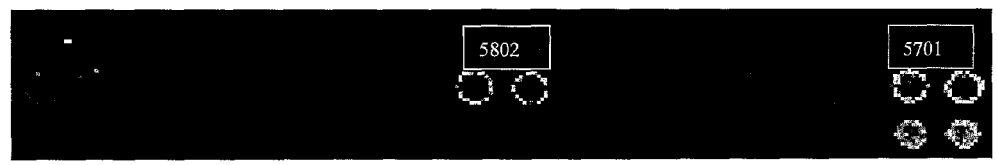
FIG. 8 shows the hybridization array using of DNAs hybridized using a normal probe and an artificially mutated probe wherein the artificial mutation site is separated from the natural SNP by a 6-mer nucleotide.

This probe only matched with HLA-B57 and B58. As shown in FIG. 8, only the standard sample B5802/4703 and B5701 gave positive signals, the other samples all gave negative signals. The optimization experiments indicate that the signal intend to become weaker and more unstable if the artificial mutation site is separated from SNP by <6.

Example 4

In this example, standard DNAs from IHWG were detected using a normal probe and an artificially mutated probe wherein the artificial mutation site is separated from the natural SNP site by a 9-mer oligonucleotide.

```
Probe Sequence:                                            5'-GGcTCTCACACCCTCCAGA-3'
                                                           (SEQ ID NO: 18)

The alleles which perfectly matched with the probe:        --G------------------

The alleles which have one base mismatch with the probe    --G--------A---------
```

Figure 9:
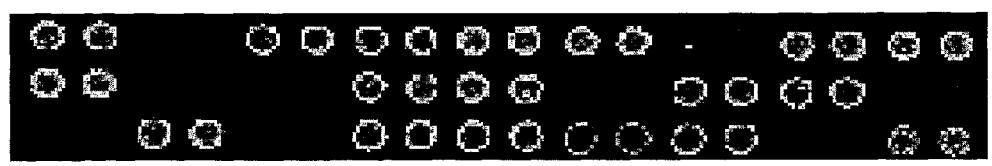
FIG. 9 shows the hybridization array using of DNAs hybridized using a normal probe and an artificially mutated probe wherein the artificial mutation site is separated from the natural SNP by a 9-mer nucleotide.

This probe matched with B7, B15, B27, and B5802 also is matched with this probe. The probe mismatched with B5701. FIG. 9 shows that the specificity is very good. The specificity was lower when compared with hybridization results wherein artificial mutation site was separated from SNP by >9.

As illustrated in these examples, sequence specific oligonucleotide probes can greatly enhance the discrimination of single nucleotide polymorphisms (SNP). Thus, artificial mutated probes may be used to discriminate mismatched base pairs and duplexes, and may be used for gene typing, such as in HLA typing.

It is understood that the foregoing detailed description and accompanying examples are merely illustrative, and are not to be taken as limitations upon the scope of the invention. Various changes and modifications to the disclosed embodiments will be apparent to those skilled in the art, and may be made without departing from the spirit and scope thereof. U.S. patents and publications referenced herein are incorporated by reference.

---

The invention claimed is:

1. A process for hybridizing an oligonucleotide to a first nucleic acid target, the method comprising the steps of:
  providing an oligonucleotide comprising a nucleic acid sequence complementary in part to the first target, but comprising at least one artificial mismatch relative to the first target and comprising a nucleic acid sequence complementary in part to a second target, but comprising at least one artificial mismatch and a true mismatch relative to the second target,
  wherein the true mismatch and the artificial mismatch are separated from one another by six to nine nucleotide positions and wherein the artificial mismatch is a naturally occurring nucleotide base; and
  combining the oligonucleotide and the first and second targets under a hybridization condition that allows formation of (a) a first duplex comprising the oligonucleotide and the first target, and (b) a second duplex comprising the oligonucleotide and the second target, wherein the first duplex has a melting temperature 4-10° C. higher than that of the second duplex.

2. The process of claim 1, wherein said oligonucleotide comprises an artificially mismatched base pair relative to said first and second target.

3. The process of claim 2, wherein said artificially mismatched base pair is AA, AC, AG, TT, TC, TG, CC, CA, CT, GG, GA or GT.

4. The process of claim 1, wherein said oligonucleotide comprises a naturally occurring nucleotide base that has been additionally inserted or deleted relative to the first and second target.

5. The process of claim 1, wherein said oligonucleotide comprises 11 to 70 nucleotides.

6. The process of claim 5, wherein said oligonucleotide comprises 15-25 nucleotides.

7. The process of claim 1, wherein the true mismatch and the artificial mismatch are separated from one another by six nucleotide positions.

8. The process of claim 1, wherein the true mismatch and the artificial mismatch are separated from one another by seven nucleotide positions.

9. The process of claim 1, wherein the true mismatch and the artificial mismatch are separated from one another by eight nucleotide positions.

10. The process of claim 1, wherein the true mismatch and the artificial mismatch are separated from one another by nine nucleotide positions.

11. A process for discriminating between a first nucleic acid target and a second nucleic acid target in a test sample, wherein the second nucleic acid target has a sequence variation relative to the first target, the process comprising the steps of:

providing an oligonucleotide comprising a nucleic acid sequence complementary in part to the first target, including at the position of the sequence variation, but comprising an artificially mismatched naturally occurring nucleotide base relative to the targets at a position other than that of the sequence variation, the artificially mismatched base and the sequence variation position being separated from one another on the oligonucleotide by six to nine nucleotide positions;

combining the oligonucleotide and the test sample under a hybridization condition that allows formation of a product selected from the group consisting of (a) a first duplex comprising the oligonucleotide and the first target, (b) a second duplex comprising the oligonucleotide and the second target and being less stable than the first duplex, and (c) a mixture comprising both the first duplex and the second duplex, wherein the first duplex has a melting temperature 4-10° C. higher than that of the second duplex;

selectively detecting the first duplex comprising the oligonucleotide and the first target or the second duplex comprising the oligonucleotide and the second target.

12. The process of claim 11, wherein said oligonucleotide comprises a naturally occurring nucleotide base that has been additionally inserted or deleted relative to the first and second target.

13. The process of claim 11, wherein said oligonucleotide comprises 11 to 70 nucleotides.

14. The process of claim 13, wherein said oligonucleotide comprises 15-25 nucleotides.

15. The process of claim 11, wherein the sequence variation position and the artificially mismatched base are separated from one another by six nucleotide positions.

16. The process of claim 11, wherein the sequence variation position and the artificially mismatched base are separated from one another by seven nucleotide positions.

17. The process of claim 11, wherein the sequence variation position and the artificially mismatched base are separated from one another by eight nucleotide positions.

18. The process of claim 11, wherein the sequence variation position and the artificially mismatched base are separated from one another by nine nucleotide positions.

* * * * *

SEQUENCE LISTING

```
<160> NUMBER OF SEQ ID NOS: 20

<210> SEQ ID NO 1
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 1
ggcatcaggc cgccccagct ccgtcaccgc ccggaactcc cccacgtcgc tgtcgaagcg    60
cacggactc                                                           69

<210> SEQ ID NO 2
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 2
ggcatcaggc cgccccagct ccgtcaccgc ccggtactcc cccacgtcgc tgtcgaagcg    60
cacggactc                                                           69

<210> SEQ ID NO 3
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
```

```
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 3
ggcatcaggc cgccccagct ccgtcaccgc ccggcactcc cccacgtcgc tgtcgaagcg    60
cacggactc                                                            69

<210> SEQ ID NO 4
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 4
ggcatcaggc cgccccagct ccgtcaccgc ccgggactcc cccacgtcgc tgtcgaagcg    60
cacggactc                                                            69

<210> SEQ ID NO 5
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 5
taggtgtcca ccgcggcccg cctctgctcc aggaagtcct tctggctgtt ccagtactcg    60
gcatcaggc                                                            69

<210> SEQ ID NO 6
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 6
taggtgtcca ccgcggcccg cctctgctcc aggatgtcct tctggctgtt ccagtactcg    60
gcatcaggc                                                            69
```

```
<210> SEQ ID NO 7
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 7
taggtgtcca ccgcggcccg cctctgctcc aggacgtcct tctggctgtt ccagtactcg     60
gcatcaggc                                                             69

<210> SEQ ID NO 8
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 8
taggtgtcca ccgcggcccg cctctgctcc aggaggtcct tctggctgtt ccagtactcg     60
gcatcaggc                                                             69

<210> SEQ ID NO 9
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 9
agtatctgtc caggaaccgc acccgctccg tcccattgaa gaaatgacac tccctcttag     60
gctgccaca                                                             69

<210> SEQ ID NO 10
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
```

```
<222> LOCATION: 35
<223> OTHER INFORMATION: SNP site

<400> SEQUENCE: 10
agtatctgtc caggaaccgc acccgctccg tccctttgaa gaaatgacac tccctcttag    60
gctgccaca                                                           69

<210> SEQ ID NO 11
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 11
agtatctgtc caggaaccgc acccgctccg tccccttgaa gaaatgacac tccctcttag    60
gctgccaca                                                           69

<210> SEQ ID NO 12
<211> LENGTH: 69
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(69)
<223> OTHER INFORMATION: HLA sequence
<220> FEATURE:
<221> NAME/KEY: misc_feature
<222> LOCATION: 35
<223> OTHER INFORMATION: SNP site

<400> SEQUENCE: 12
agtatctgtc caggaaccgc acccgctccg tcccgttgaa gaaatgacac tccctcttag    60
gctgccaca                                                           69

<210> SEQ ID NO 13
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: normal probe

<400> SEQUENCE: 13
tgggggagtt ccgggcggt                                                19

<210> SEQ ID NO 14
<211> LENGTH: 20
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(20)
```

<223> OTHER INFORMATION: artificially mutated probe
<220> FEATURE:
<221> NAME/KEY: misc_feature
<222> LOCATION: 15
<223> OTHER INFORMATION: artificially inserted cytosine

<400> SEQUENCE: 14
tgggggagtt ccggcgcggt                                                         20

<210> SEQ ID NO 15
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: normal probe

<400> SEQUENCE: 15
ggaacacacg gaaagtgaa                                                          19

<210> SEQ ID NO 16
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: artificially mutated probe
<220> FEATURE:
<221> NAME/KEY: misc_feature
<222> LOCATION: 3
<223> OTHER INFORMATION: artificially inserted cytosine

<400> SEQUENCE: 16
ggcacacacg gaaagtgaa                                                          19

<210> SEQ ID NO 17
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: normal probe
<220> FEATURE:
<221> NAME/KEY: misc_feature
<222> LOCATION: 16
<223> OTHER INFORMATION: SNP site

<400> SEQUENCE: 17
tattgggacg gggagagac                                                          19

<210> SEQ ID NO 18
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: normal probe
<220> FEATURE:
<221> NAME/KEY: misc_feature

```
<222> LOCATION: 3
<223> OTHER INFORMATION: SNP site

<400> SEQUENCE: 18
ggctctcaca ccctccaga                                                  19

<210> SEQ ID NO 19
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: normal probe
<220> FEATURE:
<221> NAME/KEY: misc_feature
<222> LOCATION: 10
<223> OTHER INFORMATION: SNP site

<400> SEQUENCE: 19
ggctatccga tcctggcct                                                  19

<210> SEQ ID NO 20
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)...(19)
<223> OTHER INFORMATION: target sequence
<220> FEATURE:
<221> NAME/KEY: misc_feature
<222> LOCATION: 10
<223> OTHER INFORMATION: SNP site

<400> SEQUENCE: 20
cctataggct aggaccgga                                                  19
```